(12) United States Patent
Groteke

(10) Patent No.: US 9,345,872 B2
(45) Date of Patent: May 24, 2016

(54) CONDUCTIVE ELECTRICAL GARMENT

(71) Applicant: Walter M. Groteke, Safety Harbor, FL (US)

(72) Inventor: Walter M. Groteke, Safety Harbor, FL (US)

( * ) Notice: Subject to any disclaimer, the term of this patent is extended or adjusted under 35 U.S.C. 154(b) by 21 days.

(21) Appl. No.: 14/035,859

(22) Filed: Sep. 24, 2013

(65) Prior Publication Data

US 2014/0083434 A1    Mar. 27, 2014

Related U.S. Application Data

(60) Provisional application No. 61/705,330, filed on Sep. 25, 2012.

(51) Int. Cl.
| | |
|---|---|
| *A61N 1/00* | (2006.01) |
| *A61N 1/04* | (2006.01) |
| *A61F 5/56* | (2006.01) |
| *A61N 1/36* | (2006.01) |

(52) U.S. Cl.
CPC .............. *A61N 1/0484* (2013.01); *A61F 5/56* (2013.01); *A61N 1/0456* (2013.01); *A61N 1/0476* (2013.01); *A61N 1/0488* (2013.01); *A61N 1/3601* (2013.01); *A61N 1/36014* (2013.01); *A61N 1/36021* (2013.01)

(58) Field of Classification Search
CPC . A61N 1/0484; A61N 1/0492; A61N 1/0456; A61N 1/0452
USPC .......................................... 607/149; 600/388
See application file for complete search history.

(56) References Cited

U.S. PATENT DOCUMENTS

| | | | | |
|---|---|---|---|---|
| 5,948,013 | A | * | 9/1999 | Swezey .................. A47C 7/425 5/636 |
| 7,072,721 | B1 | | 7/2006 | Trent |
| 2002/0077689 | A1 | * | 6/2002 | Kirkland .............. A61N 1/0452 607/149 |
| 2008/0147143 | A1 | * | 6/2008 | Popovic ............... A61N 1/0452 607/48 |
| 2008/0163428 | A1 | * | 7/2008 | Groteke et al. .................... 5/638 |
| 2009/0132018 | A1 | * | 5/2009 | DiUbaldi ............. A61N 1/0456 607/152 |

FOREIGN PATENT DOCUMENTS

WO    WO2010140823    12/2010

OTHER PUBLICATIONS http://www.target.com/p/carex-lumbar-support-cushion-with-memory-foam/-/A-11158436?ref=tgt_adv_XSG10001&AFID=Google_PLA_df&LNM=%7C11158436&CPNG=Health+Beauty&kpid=11158436&LID=PA&ci_src=17588969&ci_sku=11158436&gclid=CJXixcKWm7kCFfFj7Aod7HYAOA.
http://www.medi-stim.com/electrodes/cev.html.

* cited by examiner

*Primary Examiner* — Christopher D Koharski
*Assistant Examiner* — Philip C Edwards
(74) *Attorney, Agent, or Firm* — CIONCA Law Group P.C.; Marin Cionca

(57) ABSTRACT

An apparatus for electrical stimulation therapy comprising a garment and a plurality of electrode pads associated with the garment, wherein the electrode pads are positionable at selectable locations relative to the garment, such that to correspond to a person's body shape and areas that need electrical stimulation therapy, and wherein contact between the plurality of electrode pads and the person's body is achieved by the person resting on top of the plurality of electrode pads and garment, such that the person's weight assists in creating the contact between the plurality of electrode pads and the person's body.

13 Claims, 6 Drawing Sheets

CONDUCTIVE ELECTRICAL GARMENT

CROSS-REFERENCE TO RELATED APPLICATIONS

This application claims the benefit of U.S. Provisional Application No. 61/705,330, filed Sep. 25, 2012, which is hereby incorporated by reference, to the extent that it is not conflicting with the present application.

BACKGROUND OF THE INVENTION

1. Field of the Invention

The invention relates generally to the treatment of neuromusculoskeletal conditions by use of transcutaneous electrical stimulation modalities and more particularly to methods and systems for such treatment using a conductive electrical garment.

2. Description of the Related Art

Electrical stimulation modalities, such as transcutaneous electrical nerve stimulations ("TENS"), are common techniques used to reduce the amount of pain and inflammation experienced by patients. It sends electrical impulses through the neuromusculoskeletal system to block pain signals, improve circulation and promote healing in patients.

Typically, electrical stimulation devices operate with two electrode pairs, for a maximum of four pads at a time. This allows a user to apply electrical stimulation at up to two sections of their body (usually in positions that are "linked" to the specific type of pain experienced).

Most electrical stimulation devices (e.g., TENS units, muscle stimulation devices, etc) use some form of adhesive to ensure contact between the electrode pad and the user's skin. This is not only uncomfortable to the user/patient, but the adhesive effect will eventually wear off and require replacement of the pads. Further, it is difficult for a user to place and apply these electrodes/pads on difficult to reach areas of the body. An example would be the placement on one's back or neck. This is especially difficult to apply when an individual is in pain.

Other electrical stimulation devices use constrictive electrical garments, which are inconvenient to the user/patient. Examples are back braces and vests with electrode/pads.

None of these devices provide a solution where a user can simply and freely position themselves on a resistive, pressure relieving orthopedic material, which holds them in the correct posture while getting the intended benefits of electrical stimulation.

Furthermore, the existing devices do not appear to easily, comfortably and effectively allow for a combination with orthopedic devices (e.g., orthopedic pillows) so that a user/patient may benefit from a combined and simultaneous treatment. When a patient/individual is in pain, and she seeks electrical stimulation for pain relief for example, there is a high probability that the pain is being caused by a misalignment of the skeletal system. By using the traditional method of electrical stimulation, you are stimulating an area that may have a muscular/skeletal misalignment, which could be the source of pain or referring pain to other parts of the body. It would be much more effective to use electrical stimulation in conjunction with an orthopedic device, such as an orthopedic pillow or lumbar support pillow, so that one can ensure that an individual is maintaining proper posture or muscular skeletal alignment during electrical stimulation. Providing various types of electrical stimulation to these affected areas, in conjunction with an orthopedic device, may improve blood flow to assist in pain relief and healing to that region, as well reducing potential impinged nerves. In addition, this solution may promote proper muscle memory thereby improving the integrity of the muscular skeletal region/system.

Thus, there is a need for a new and improved apparatus, system and method that solve the above problems.

The problems and the associated solutions presented in this section could be or could have been pursued, but they are not necessarily approaches that have been previously conceived or pursued. Therefore, unless otherwise indicated, it should not be assumed that any of the approaches presented in this section qualify as prior art merely by virtue of their presence in this section of the application.

BRIEF SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In one exemplary embodiment, a resistive pillow/bedding may use the weight of the patient to provide a firm, steady point of contact between electrode pads of a conductive electrical cover and the patient's skin. Thus, an advantage is eliminating the requirement for an adhesive material that will eventually need replacing as its adhesive properties wear off.

In another exemplary embodiment, a pillow/bedding cover may have a network of evenly-spaced eyelets that would allow for the electrode wires to run underneath the cover and interface with the electrode pad at the desired location. Thus an advantage is a "one size fits all" product that may possess a high degree of adjustability concerning pad location to account for example for the different body shapes of various patients.

In another exemplary embodiment, the invention may operate with various orthopedic cushioning devices. Such devices may include head and neck pillows, lumbar support pillows, leg wedges, and full-body bedding. The effectiveness of these orthopedic devices, when combined with a conductive electrical cover, may be greatly improved.

In another exemplary embodiment, the use of electrical stimulation modalities may assist in the elimination of snoring or sleep apnea when paired with a proper orthopedic head rest. By providing nervous stimulation to a properly oriented neck, the invention may be capable of assisting in the repair of soft tissue structures in the anterior portion of the neck and upper torso, which includes constricted airways. Over a period of time, the electrical stimulation modalities may result in a greatly improved airway channel for patients suffering from obstructive sleep apnea or snoring.

In an alternative embodiment, air bladders or air bags may be used to improve the effectiveness of the pillow, bedding and/or the conductive electrical garment. This allows for better positioning of the relevant regions of the musculoskeletal system which consequently improves the effectiveness of using electrical stimulation devices.

The above embodiments and advantages, as well as other embodiments and advantages, will become apparent from the ensuing description and accompanying drawings.

BRIEF DESCRIPTION OF THE DRAWINGS

For exemplification purposes, and not for limitation purposes, embodiments of the invention are illustrated in the figures of the accompanying drawings, in which.

DETAILED DESCRIPTION OF THE PREFERRED EMBODIMENTS

Figure 1:
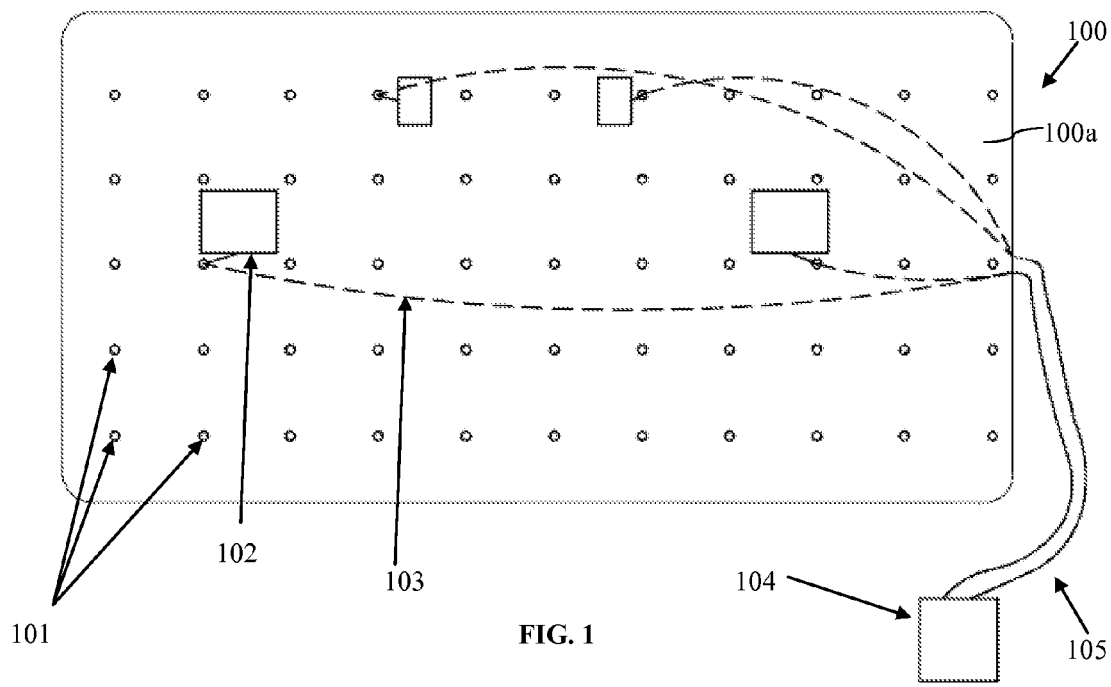
FIG. 1 illustrates the top view of a conductive electrical pillow cover with possible pad placement, according to an embodiment.

What follows is a detailed description of the preferred embodiments of the invention in which the invention may be practiced. Reference will be made to the attached drawings, and the information included in the drawings is part of this detailed description. The specific preferred embodiments of the invention, which will be described herein, are presented for exemplification purposes, and not for limitation purposes. It should be understood that structural and/or logical modifications could be made by someone of ordinary skills in the art without departing from the scope of the invention. Therefore, the scope of the invention is defined by the accompanying claims and their equivalents.

For the following description, it can be assumed that most correspondingly labeled structures across the figures (e.g., 200 and 300, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

FIG. 1 illustrates the top view of a conductive electrical pillow cover (element 100) with possible pad placement, according to an embodiment. As shown, the pillow cover 100 may have a network of small eyelets 101 spaced evenly apart vertically and horizontally in a structured grid. The spacing and quantity of eyelets may vary, but preferably they are arranged in structured rows and columns. This arrangement allows for an easy interface between the electrode wires 103 and the electrode pads 102 themselves, and offer great versatility in pad placement that is independent of the patient's shape or size or pain location. As a result, custom fitting of a conductive electrical pillow cover for each patient may not be required, which may lead to greater affordability and easier manufacturing. The interfacing electrode wires 103 run preferably underneath the conductive electrical pillow cover and originate from a pair of lead wires (element 105) that connect to the TENS control unit (or other electrical stimulation device) 104. The TENS control unit (or other electrical stimulation device) 104 powers the electrode pads 102 and allows the user to adjust the intensity of the current that runs through the pads. Typically, a patient will only need to use one TENS control unit; however two or more TENS units 104 may also be used, such as when the TENS unit is configured to power only four electrode pads and the user wishes to use more than four electrode pads.

The electrode pads 102 may be made, for example, entirely from conductive, woven, fabric material or from foam wrapped in the conductive, woven, fabric material. Other suitable conductive materials may be used for the electrode pads 102 as well. The conductive, woven, fabric material may be woven fabric(s) such as nylon and conductive/metallic threads (e.g., silver). The conductive/metallic threads may be separated from the user/patient's skin by layers of nonconductive fabric. The structural element 100*a* of the conductive electrical cover/garment 100 may be, for example, a sheet of, for example, neoprene, or other suitable garment, and is typically nonconductive. In an alternative embodiment, the structural element 100*a* may be conductive, made for example from a conductive, woven, fabric material described above, such as when the objective would be to eliminate the need to use the electrode wires 103 and instead electrically connect a plurality of eyelets (e.g., each odd number row) to one of the lead wires 105 and a plurality of eyelets (e.g., each even number row) to the other lead wire 105, by using for example woven metallic threads. In this case the electrode pads 102 would need to be electrically connected directly with the appropriate eyelet 101. It should be apparent that the eyelets 105 would also need to be conductive in this alternative embodiment. Further, the eyelets 105 may be color coded (a different color for each lead wire 105) and may for example be magnetic, for easy connection and securing of electrode pads 102.

Again, as shown, electrode wires 103 may be used to connect the TENS unit (or other electrical stimulation device) 104 to the electrode pads 102. However, a wireless system may also be used. Such a system may for example include battery-powered electrode pads that receive signals from a remote control TENS unit that can power on the pads and adjust their intensity. This may avoid the hassle of threading wires underneath the cover and through the eyelets (eliminating thus the need for eyelets altogether), and allow for even easier and more versatile placement of electrode pads.

Figure 2:
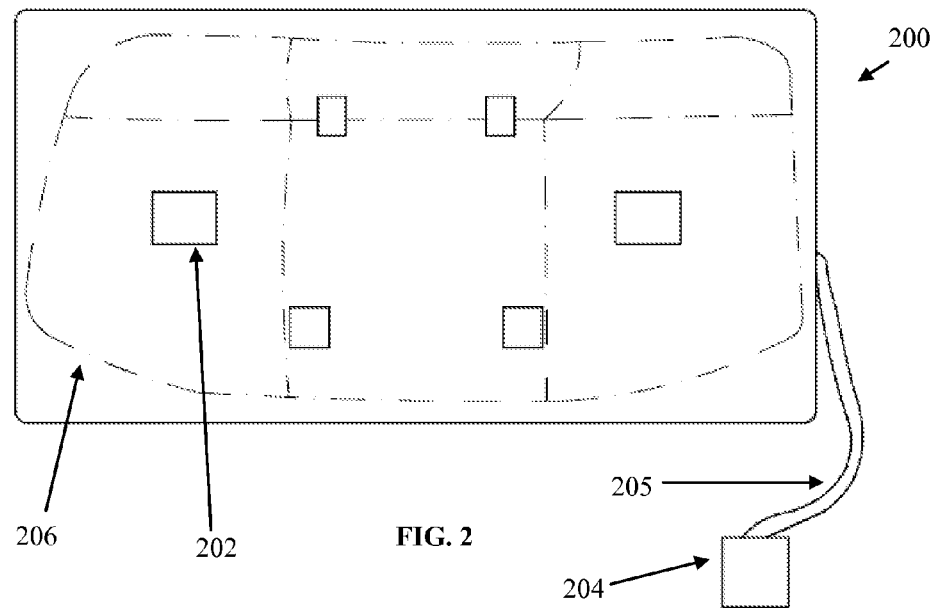
FIG. 2 illustrates the top view a conductive electrical pillow cover for an orthopedic pillow, according to another embodiment.

FIG. 2 illustrates the top view of a conductive electrical pillow cover 200 for an orthopedic pillow (element 206), according to another embodiment. In this figure, and all subsequent figures, the network of eyelet holes (element 101 of FIG. 1) have been omitted from the drawings for the sake of visual clarity and thus it should be assumed to be optionally present whenever a conductive electrical cover/garment is shown. Alternatively, for example, the electrode pads 202 may be attached with for example hook-and-loop fastener or other suitable attaching means and the electrode wires (103 in FIG. 1) may then be run on top or underneath of the conductive electrical pillow cover 200.

In this figure (FIG. 2), as shown, the displayed electrode pads (element 202) add up to six. Currently, TENS units appear to support a maximum of four electrodes (two pairs), but this may change as technology progresses. Thus, if a user/patient requires more than four pads for relief, and she is in possession of a plurality of four-pad units, or a unit that supports more than four pads, the conductive electrical pillow/bedding garment is capable of supporting the additional electrodes.

The outline of a pillow 206, which may be the pillow described in U.S. Pat. No. 7,546,651, which is incorporated by reference herein, is shown. The conductive electrical pillow cover 200 may encapsulate the entire pillow, optionally fastening itself with for example a zipper mechanism or tie-strings to prevent the pillow from sliding out. The TENS unit (element 204) and lead wires (element 205) are explicitly shown, but, for clarity of the drawing, the interfacing electrode wires (103 in FIG. 1) have been omitted from FIG. 2 (also from FIGS. 5-10), and can be assumed to be present in the design, if wire connections are used (as opposed to wireless connections as described earlier).

The conductive electrical pillow cover 200 may be configured to perfectly fit a particular pillow design, such as the orthopedic pillow described in U.S. Pat. No. 7,546,651, or it may be configured to be more universal and thus be able to cover a plurality of typical shapes and sizes of pillows, whether orthopedic or not. Tie-strings (not shown), or other suitable means, may be used to allow a user to snugly secure the conductive electrical pillow cover 200 to the pillow 206.

Figure 3:
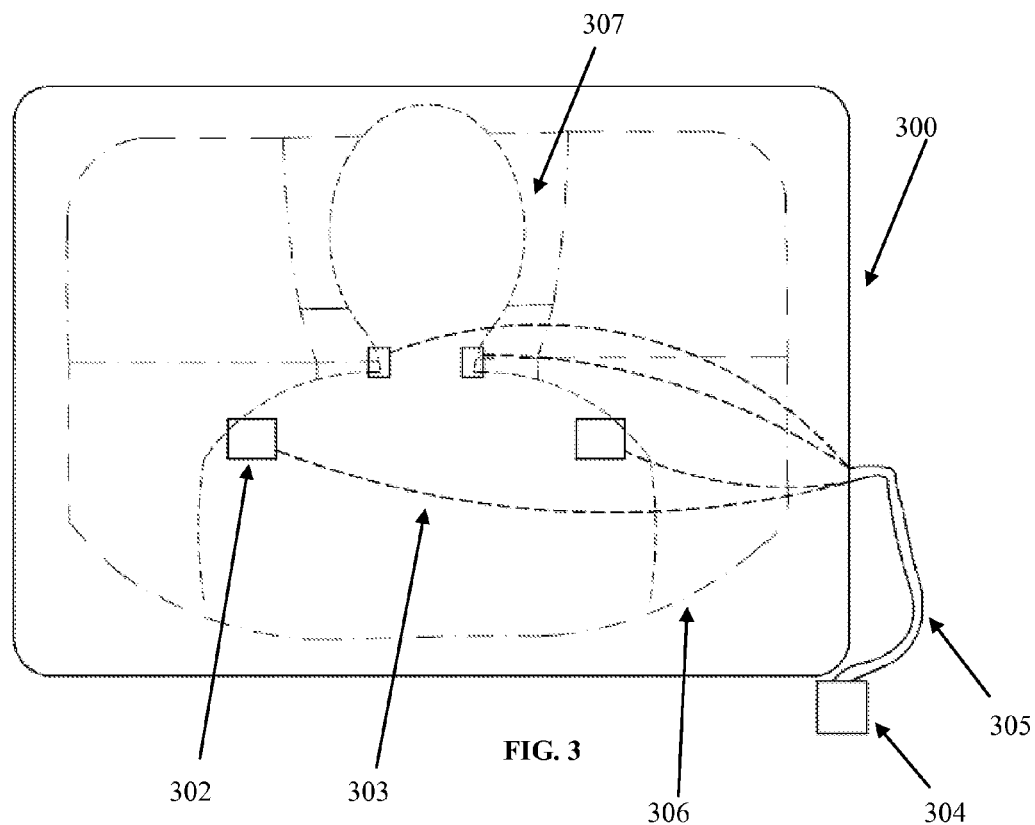
FIG. 3 illustrates the top view of the conductive electrical pillow cover and orthopedic pillow from FIG. 2, with the addition of the outline of a human upper body.

FIG. 3 illustrates the top view of the conductive electrical pillow cover 300 and an orthopedic pillow from as in FIG. 2, with the addition of the outline of a human upper body 307. The patient's body is key to the operation of the conductive electrical pillow cover 300. Rather than relying on adhesive material to interface the electrode pads 302 with the patient's skin, the user/patient's weight, as the patient rests on the pillow 306, or on other bedding or orthopedic device, may result in a clean and effective connection between electrode and skin. Consequently, all electrode pads 302 should be located by the user/patient or his medical professional underneath the patient's body, and corresponding to the area that need treatment, to ensure that this weight mechanism is functioning properly. A TENS unit (element 304) and lead wires (element 305) extend out into electrode wires (element 303) that may also run underneath the patient's body, and preferably underneath of cover 300, but they may not be felt by the user/patient due to the elastic properties of the pillow/bedding material (e.g., memory foam).

The use of the patient's body weight is advantageous, as the use of adhesive material to attach electrodes to the body requires regular replacement of pads. Over the course of normal use, the pads lose their adhesive qualities and fresh pads are needed if the patient wishes to continue using the device. Certain conditions, such as applying the adhesive to dirty or wet skin, applying the adhesive over body hair, etc., may even reduce the lifespan of the adhesive material further. Without the need to worry about electrode adhesion, the conductive electrical pillow cover 300 is capable of creating a clean connection regardless of where the pads 302 are placed, so long as they remain underneath the patient.

Additionally, bedding and pillows made out of ideal resistive material (such as memory foam) may have the ability to easily flex when the wires are pushed down by the weight of the patient, resulting in wiring that is unnoticeable by the patient.

As shown in FIG. 3, two pairs (four pads) of electrode pads 302 are used in this example, one for the neck and one for the shoulders. It should be understood, that, as described earlier, more than four pads may be used, so that more areas are simultaneously treated. Thus, for example, a user/patient or his doctor could install two additional pads for the head are and/or two additional pads for the upper back area.

Figure 4:
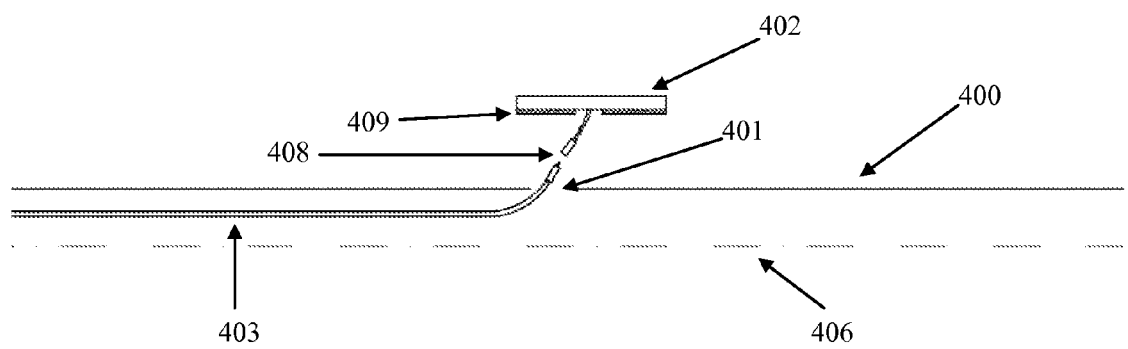
FIG. 4 illustrates a sectional view of a pillow and a conductive electrical pillow cover that demonstrates how the wiring will interface with the electrode pads, according to an embodiment.

FIG. 4 illustrates a sectional view of a pillow and cover system that shows how the wiring will interface with the electrode pads. The interface/electrode wire (element 403) runs preferably as shown underneath the conductive electrical pillow cover 400 and above the resistive pillow material (element 406), for more convenience to the user/patient. Once the wire 403 reaches the location of the electrode pad (402), it is threaded through the closest eyelet hole (element 401) so that it may interface with the electrode pad via connectors 408. The connector 408 shown in the figure (male-female connector) is merely an example, and the type of connectors that may be used is not limited to that which is displayed. Optionally, the electrode pad 402 may possess some way to firmly fasten itself to the cover, such as with fabric hook-and-loop fasteners (element 409) located on its underside.

Figure 5:
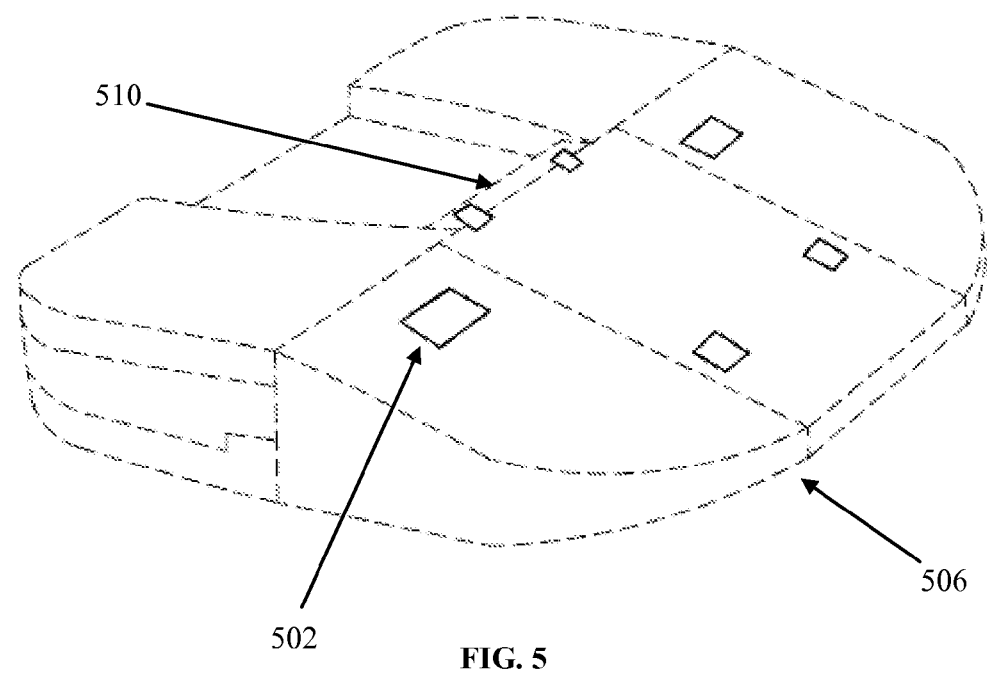
FIG. 5 illustrates a perspective view of an orthopedic pillow and a possible pad placement, according to an embodiment.

FIG. 5 illustrates a perspective view of an orthopedic pillow 506 described in U.S. Pat. No. 7,546,651, which is incorporated by reference herein, and exemplary pad placement (element 502). Orthopedic cushions are the preferable base for the conductive electrical pillow cover (the cover was omitted from the figure, as well as the wires, for clarity of the drawing), and the pillow described in U.S. Pat. No. 7,546,651 ("Atlast™" pillow) is an example of orthopedic devices having such cushions. Orthopedic cushions generally promote better posturing and regional stability of the body's neuro-musculoskeletal system, and therefore creating an environment for optimal healing while a patient is receiving a particular electrical stimulation modality. Furthermore, this optimal and regionally stable environment allows the neuro-musculoskeletal system to relax and better accept modalities for optimal healing. In the case of the Atlast™ pillow, proper resting position of the head, among other benefits, may be achieved.

An additional benefit of using the conductive electrical pillow cover with an Atlast™ pillow may be the ability to assist patients who suffer from obstructive sleep apnea or snoring. The section of the pillow supporting the cervico-cranial region of the neck (element 510) is designed to allow for optimal posturing of the head and neck. When this advantage is combined with the TENS therapy provided by the conductive electrical pillow cover and electrode pads 502, it may improve circulation and innervation in the region's musculature. The result may be a more efficient repair of the region's soft tissue and increased cervico-cranial stability. This may have especially positive effects on patients suffering from snoring or obstructive sleep apnea.

By providing electrical stimulation to the cervical region, while positioning a user/patient such that optimal spinal curvature is achieved, the user's cervico-cranial and cervico-thoracic regions are enhanced to propagate a relaxed and stable spinal alignment.

Through the combination of the Atlast™ orthopedic device with electrical stimulation using a conductive electrical pillow cover as described herein, improved circulation and innervation may occur, and therefore assist in enabling the region's soft tissue to more efficiently repair itself either in an acute or a chronic state. Furthermore, this combination of a cervical orthopedic support device with electrical stimulation promotes cervico-cranial stability from the occiput through the scapulo-thoracic region. As a result of this regional re-posturing, re-alignment and ultimately healing environment set up by this combination, other soft tissue structures affected are in the anterior portion of the neck. They include but are not limited to the upper, middle and lower (caudal) airways as they are re-positioned and re-postured to effect a more patent caudal airway in a regionally stabilized environment. Thus, this regional repositioning and ultimate regional healing position may result in a more patent airway in individuals where the airway may be more narrowed, such as individuals with obstructive sleep apnea or snoring.

Figure 6:
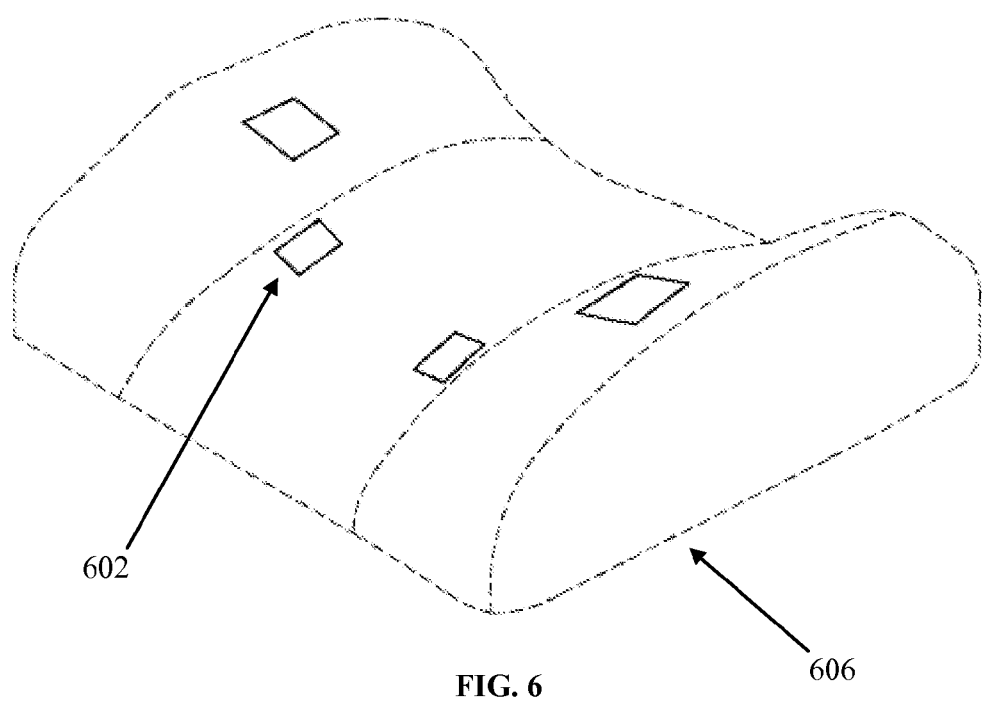
FIG. 6 illustrates a perspective view of an orthopedic lumbar support pillow and a possible pad placement, according to an embodiment.

FIG. 6 illustrates a perspective view of an orthopedic lumbar support pillow (element 606) and exemplary pad locations (element 602). Again, the cover, the wires and the TENS unit are not shown, for clarity of the drawing. Lumbar support pillows are orthopedic devices that assist with proper positioning of the lower back. The conductive electrical pillow cover (not shown), is capable of providing TENS therapy that may enhance the benefits of such a pillow. The additional benefits to the user/patient's lumbar area are similar to those described above when referring to FIG. 5 (improved circulation, improved innervation, and so on). Similar benefits may be obtained for other regions of a person body by combining the conductive electrical cover described herein with additional orthopedic devices such as wedge pillows (for either body or leg(s)), contour leg pillows, full-body cushions and so on. Different conductive electrical cover sizes may be required for different classes of orthopedic devices and/or for each device, but the cover for a specific class (e.g., orthopedic pillows) may be a one-size-fits-all as described earlier.

Further, as described earlier when referring to FIG. 1, the conductive electrical cover 100, because of the presence of the eyelets 101, provides a high degree of flexibility to the user/patient or his doctor as to where the pads 602 are specifically located in order to accommodate to patient's body shape and size and correspond to the areas that need treatment.

Figure 7:
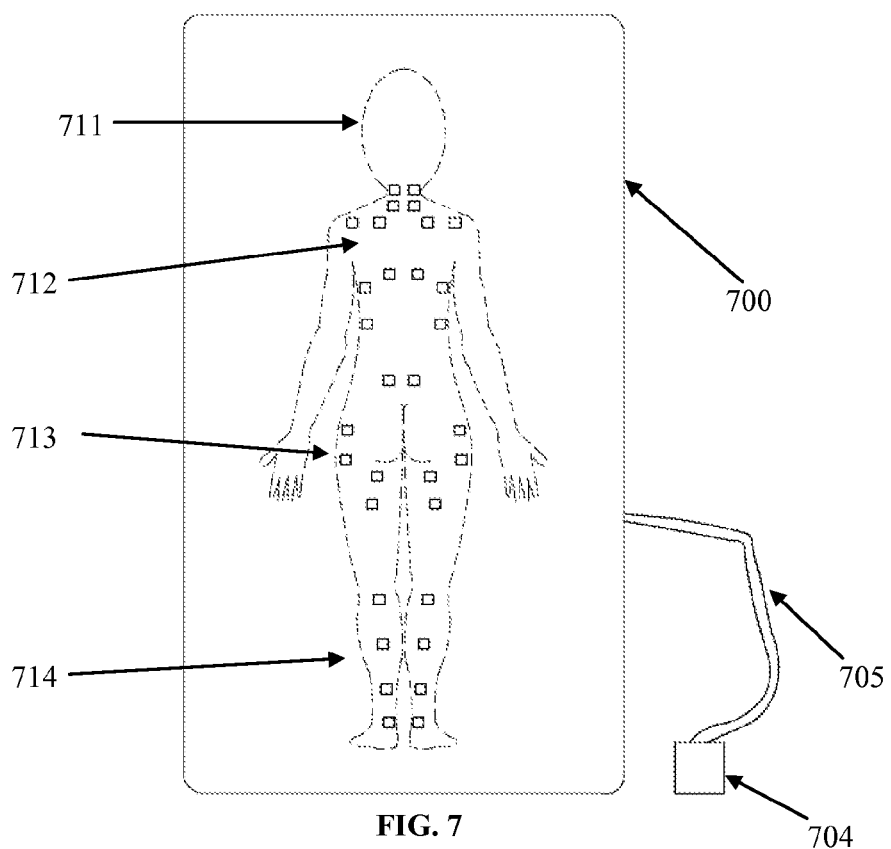
FIG. 7 illustrates a top view of a full-body cover and possible pad placement, according to an embodiment.

FIG. 7 illustrates a top view of a full-body cover/garment and possible pad placement. A full-body cover (element 700) for orthopedic bedding may be an effective way of combating numerous instances of pain. Where a smaller pillow may be able to only focus on a specific region of the body, a full-body cover may offer a large degree of versatility in providing pain relief. Given the ability to cover the entire body with its network of eyelet holes (not shown in FIG. 7 for clarity, but see 101 in FIG. 1), a patient (represented by element 711) may be able to use a single conductive electrical cover to assist in combating pain in lower extremities (element 714), mid region (element 713), and the upper body (element 712). This may be done simultaneously with a plurality of TENS units and lead wires (elements 704 and 705), or at different times without necessitating the acquisition of additional conductive electrical cover specific to each region. Due to the nature of the eyelet grid, the full-body cover may allow patients of varying body shapes and sizes to use the same conductive electrical cover without any loss in effectiveness.

Figure 8:
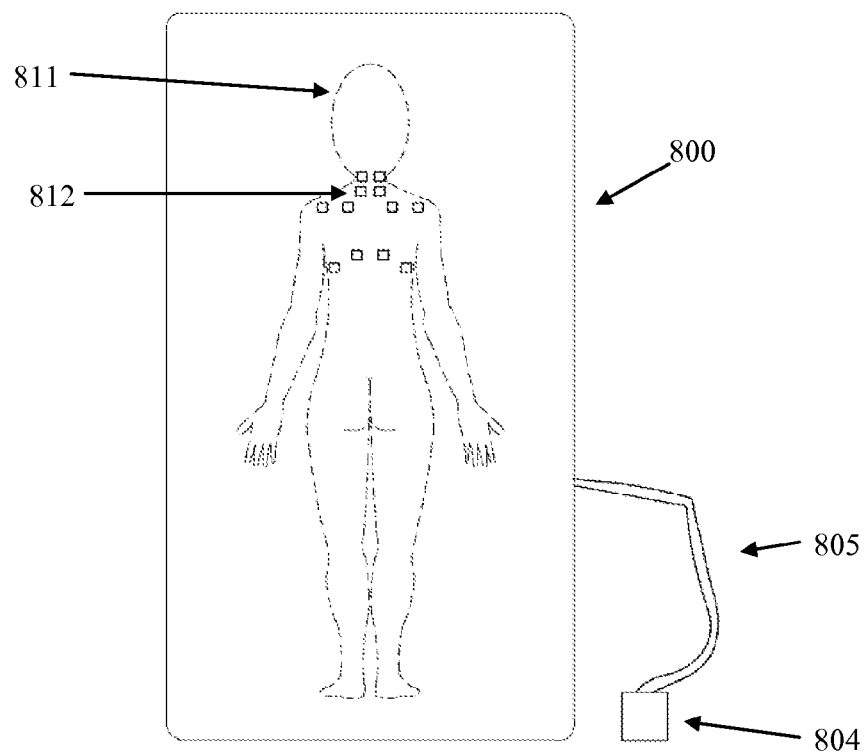
FIG. 8 illustrates the top view of a full-body cover from FIG. 7, with only upper body pad placement regions displayed.

FIG. 8 illustrates the top view of the full-body cover (element 800) for a patient (element 811), with only upper body pad placement regions (element 812) displayed. Possible types of pain associated with these regions may include shoulder and upper extremity pain, neck and bilateral shoulder pain, phantom limb pain (Upper Extremity), and pain resulting from Herpes Zoster ("Shingles"). As these are all forms of pain that can be alleviated with back placement of TENS electrodes, they may be relieved by the use of the conductive electrical bedding garment 800. A TENS unit and lead wires (elements 804 and 805) are also shown.

Figure 9:
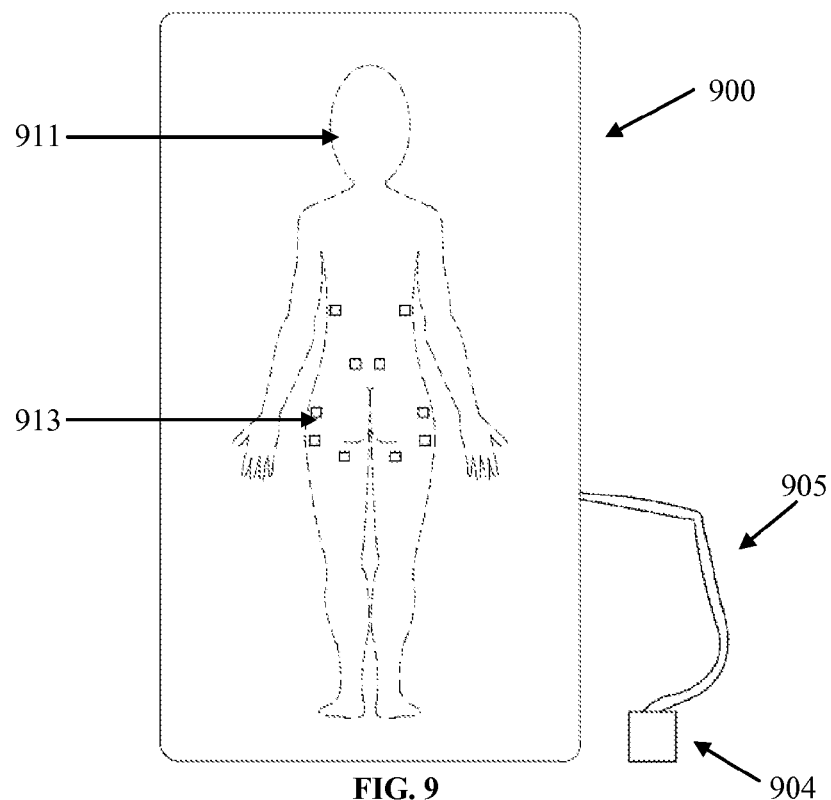
FIG. 9 illustrates the top view of a full-body cover from FIG. 7, with only mid body pad placement regions displayed.

FIG. 9 illustrates the top view of the full-body cover (element 900) for a patient (element 911), with only mid body pad placement regions (element 913) displayed. Possible types of pain associated with these regions may include Lower Back Pain, Sciatica, and pain in the Rectal, Scrotal, Vaginal, or Saddle Area. As these also are all forms of pain that can be alleviated with back placement of TENS electrodes, they may be relieved by the use of the conductive electrical bedding garment 900. A TENS unit and lead wires (elements 904 and 905) are also shown.

Figure 10:
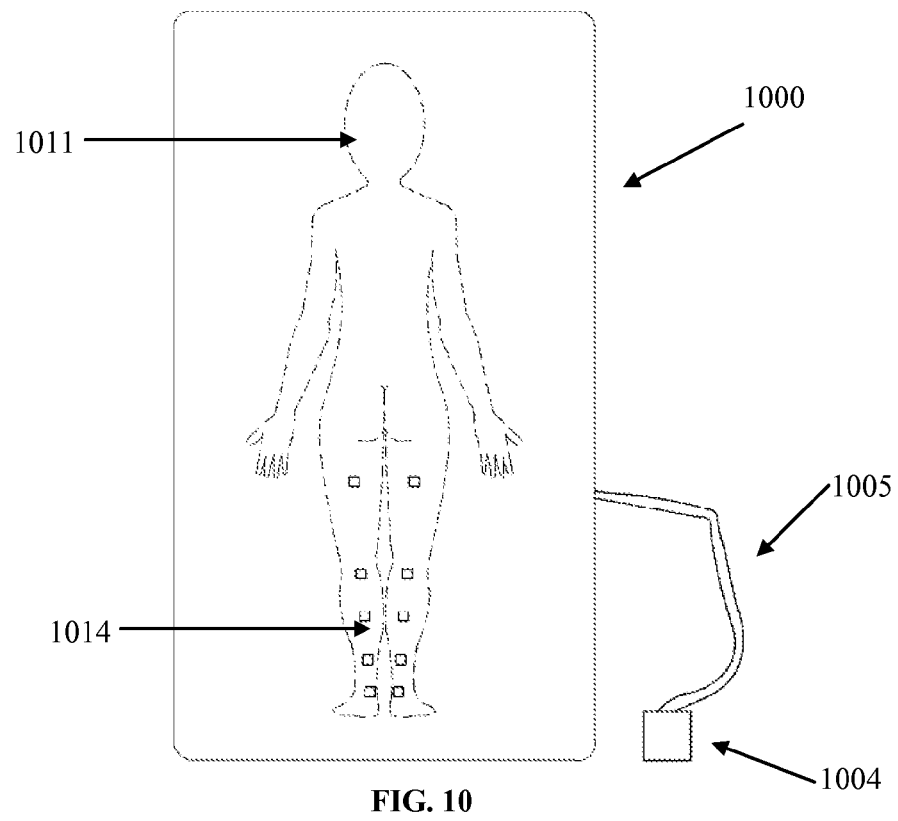
FIG. 10 illustrates the top view of a full-body cover from FIG. 7, with only lower body pad placement regions displayed.

FIG. 10 illustrates the top view of the full-body cover (element 1000) for a patient (element 1011), with only lower body pad placement regions (element 1014) displayed. Possible types of pain associated with these regions may include Bilateral Leg Pain, Phantom Limb Pain (Lower Extremity), Knee Pain, and Ankle and/or Foot pain. As these also are all forms of pain that may be alleviated with back placement of TENS electrodes, they may be relieved by the use of the conductive electrical bedding garment. A TENS unit and lead wires (elements 904 and 905) are also shown.

Figure 11:
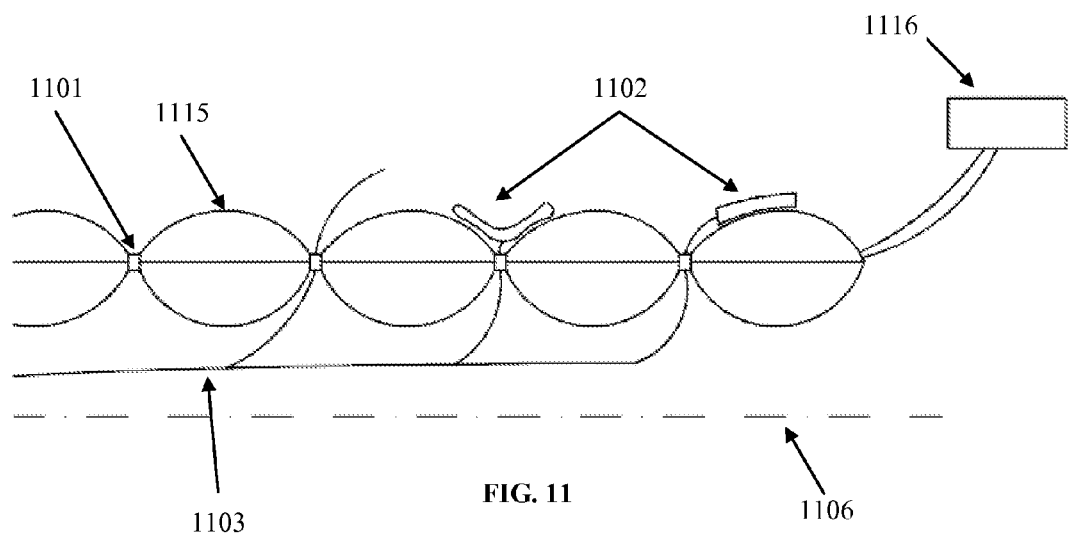
FIG. 11 illustrates a sectional view of an alternative embodiment wherein the conductive electrical cover/garment uses a system of air bladders.

FIG. 11 illustrates a sectional view of an alternative embodiment wherein the conductive electrical cover/garment uses a system of air bladders. At certain locations, or in its entirety, the conductive electrical cover may be converted into, added to, or replaced by a system of air bladders (element 1115), which are inflated by an attached pump (element 1116). The air pressure in the bladders 1115 may be adjustable by the user/patient. This may offer users/patients greater control to ensure their body is properly positioned when resting, to allow for improved contact between the electrode pads 1102 and the patient's skin, and thus, for improved efficiency of electrical stimulation therapy. Element 1101 shows the eyelets (101 in FIG. 1), which may still be evenly spaced throughout the alternate covering so that the interface/electrode wires (element 1103) located below the bladders 1115 may pass through and connect with the electrode pads (element 1102), which may be located above the bladders 1115, at various suitable relative positions, as shown. This alternative conductive electrical cover may be located above an orthopedic pillow, orthopedic bedding or another orthopedic device (element 1106).

Figure 12:
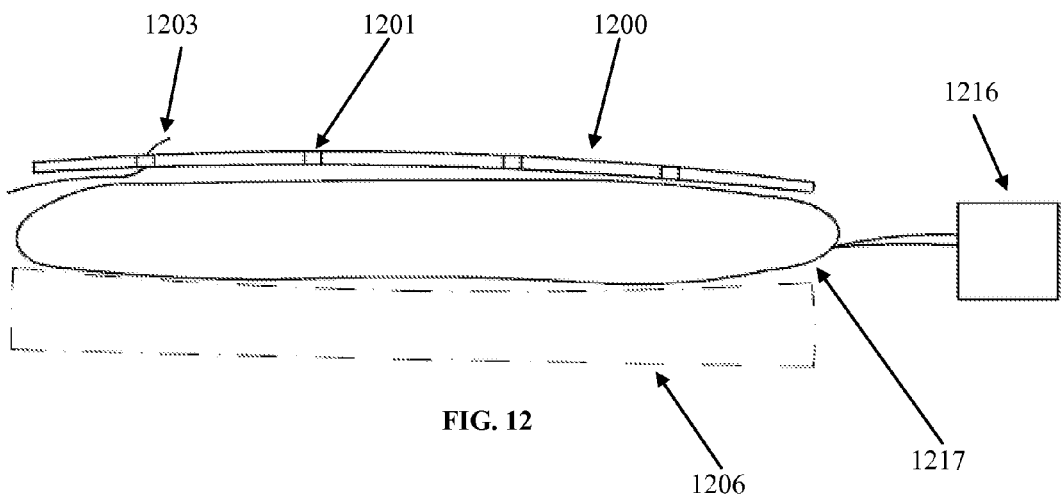
FIG. 12 illustrates a sectional view of an alternative embodiment wherein an air bag layer is added between the pillow and the conductive electrical cover.

FIG. 12 illustrates a sectional view of another alternate embodiment that may employ the use of an air bag (element 1217) that serves as an additional layer between the pillow, or other orthopedic device (element 1206), and conductive electrical cover (element 1200). The air bag may have an attached pump (element 1216) that inflates the air bag 1217 to a desirable pressure. Eyelet holes (element 1201) allow for the interface wires (element 1203) to thread through the cover and connect with the electrode pads (not shown) to provide nerve stimulation to the patient.

It should be understood that while a TENS unit and the associated TENS therapy may have been more often referred to herein, other electrical stimulation devices, where electro therapy is implicated, may similarly be used. For example, a muscle stimulator device may also be used in conjunction with the disclosed invention.

Thus, key aspects of the conductive electrical garment disclosed herein are the covering containing a grid of eyelet holes, resistive (preferably orthopedic) pillow/bedding material, and force of gravity to ensure a clean pad-to-skin contact. The covering may be adapted to any pillow, bedding, or other orthopedic cushion, and may offer substantial versatility in electrode pad placement by way of a grid of eyelet holes. This allows a patient or doctor to place the electrodes exactly where they're needed without concern for wire pathing issues, regardless of the patient's body shape, size or height, or the location of the areas that need treatment. Alternative embodiments may also allow for air bladders to either replace sections of the covering, added to, or be included underneath the cover and provide additional support for the patient and improved contact between the electrode pads and patient's skin.

Again, while any pillow/bedding may reasonably be used with the claimed covering, an orthopedic material and device is preferred due to its intended function of properly positioning the musculoskeletal system of a patient. This property of orthopedic cushions greatly enhances the effectiveness of electro therapy, as it allows the body's musculature to repair itself in a proper orientation.

The use of gravity as an alternative to adhesives for the electrode pad may avoid the need to buy replacement pads over the course of regular use of a TENS unit. By using the patient's bodyweight to ensure the pad is in firm contact with the patient's skin, a gravity-dependent pad may be used indefinitely, so long as it is located directly underneath the patient's body.

It may be advantageous to set forth definitions of certain words and phrases used in this patent document. The term "couple" and its derivatives refer to any direct or indirect communication between two or more elements, whether or not those elements are in physical contact with one another. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like.

As used in this application, "plurality" means two or more. A "set" of items may include one or more of such items. Whether in the written description or the claims, the terms "comprising," "including," "carrying," "having," "containing," "involving," and the like are to be understood to be open-ended, i.e., to mean including but not limited to. Only the transitional phrases "consisting of" and "consisting essentially of," respectively, are closed or semi-closed transitional phrases with respect to claims. Use of ordinal terms such as "first," "second," "third," etc., in the claims to modify a claim element does not by itself connote any priority, precedence or order of one claim element over another or the temporal order in which acts of a method are performed. These terms are used merely as labels to distinguish one claim element having a certain name from another element having a same name (but for use of the ordinal term) to distinguish the claim elements. As used in this application, "and/or" means that the listed items are alternatives, but the alternatives also include any combination of the listed items.

Throughout this description, the embodiments and examples shown should be considered as exemplars, rather than limitations on the apparatus and procedures disclosed or claimed. Although many of the examples involve specific combinations of method acts or system elements, it should be understood that those acts and those elements may be combined in other ways to accomplish the same objectives. Acts, elements and features discussed only in connection with one embodiment are not intended to be excluded from a similar role in other embodiments.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

Although specific embodiments have been illustrated and described herein for the purpose of disclosing the preferred embodiments, someone of ordinary skills in the art will easily detect alternate embodiments and/or equivalent variations, which may be capable of achieving the same results, and which may be substituted for the specific embodiments illustrated and described herein without departing from the scope of the invention. Therefore, the scope of this application is intended to cover alternate embodiments and/or equivalent variations of the specific embodiments illustrated and/or described herein. Hence, the scope of the invention is defined by the accompanying claims and their equivalents. Furthermore, each and every claim is incorporated as further disclosure into the specification and the claims are embodiment(s) of the invention.

What is claimed is:

1. A system for simultaneous targeting of proper musculoskeletal aligning and positioning and electrical stimulation therapy comprising an orthopedic device configured for providing musculoskeletal aligning and positioning of a person's body or part thereof and a cover that fits over the orthopedic device, the cover having a network of eyelets arranged in evenly spaced apart rows and columns, and a plurality of electrode pads, wherein the electrode pads are positionable at user selected locations relative to the cover and independently of the orthopedic device, such that to correspond to a person's body shape, the orthopedic device's shape, and areas determined by a user before use of the system as being in need of electrical stimulation therapy while musculoskeletal aligning and positioning is provided by the orthopedic device, wherein the eyelets allow the passage of wires electrically connecting the plurality of electrode pads with an electrical source, and wherein contact between the plurality of electrode pads and the person's body is achieved by the person resting on top of the plurality of electrode pads, cover, and orthopedic device, such that the person's weight assists in creating the contact between the plurality of electrode pads and the person's body.

2. The system from claim 1, wherein the electrical source is a transcutaneous electrical nerve stimulation unit.

3. The system from claim 1, wherein the electrical source is a muscle stimulator device.

4. The system from claim 1, wherein the cover is a full-body-length cover.

5. The system from claim 1, further comprising a plurality of bladders used to controllably push the plurality of electrode pads toward the person's body for proper contact, by adjusting the pressure in the plurality of bladders.

6. The system from claim 1, further comprising an air bag placed underneath the cover and used to controllably push the plurality of electrode pads toward the person's body for proper contact, by adjusting the pressure in said air bag.

7. The system from claim 1, wherein the orthopedic device is a member of a group consisting of a head and neck support device, a lumbar support device, an orthopedic bedding and a leg wedge.

8. The system from claim 1, wherein the orthopedic device is a device for supporting and positioning a head and a neck of a primate to relieve or mitigate a sleeping disorder comprising: a supportive core constructed of resilient material, with said supportive core comprising: a core Atlanto-Axial support (AXS) portion with an inclined AXS support, a shoulder ramp portion for elevating said primate's shoulders, and at least two side head support portions; an upper support layer constructed of visco-elastic material placed on top of said supportive core, with said upper support layer comprising: an upper head support portion, at least two upper side head support portions that are elevated above said upper head support portion, an upper shoulder ramp portion, and at least two upper side shoulder ramp portions; wherein said core AXS portion positions the primate's Atlanto-Axial joint at approximately 16-20 degrees while said primate is in a substantially supine position, and the primate's head is elevated at least 3 inches above the base of the apparatus.

9. The system from claim 1, wherein the plurality of electrode pads are battery-powered and wirelessly receive signals from a remote control TENS unit.

10. The system from claim 1 wherein the user is a doctor of the person who needs the electrical stimulation therapy.

11. The system from claim 1 wherein the user is the person who needs the electrical stimulation therapy.

12. A system for simultaneous targeting of proper musculoskeletal aligning and positioning and electrical stimulation therapy comprising an orthopedic device configured for providing musculoskeletal aligning and positioning of a head and a neck of a person and a cover that fits over the orthopedic device, the cover having a network of eyelets arranged in spaced apart rows and columns, and a plurality of electrode pads, wherein the electrode pads are positionable at user selected locations relative to the cover and independently of the orthopedic device, such that to correspond to a person's head and neck, the orthopedic device's shape, and areas determined by a user before use of the system as being in need of electrical stimulation therapy while musculoskeletal aligning and positioning is provided by the orthopedic device, wherein the eyelets allow the passage of wires electrically connecting the plurality of electrode pads with an electrical source, and wherein contact between the plurality of electrode pads and the person's head and neck is achieved by the person resting on top of the plurality of electrode pads, cover, and orthopedic device, such that the person's weight assists in creating the contact between the plurality of electrode pads and the person's head and neck.

13. A system for simultaneous targeting of proper musculoskeletal aligning and positioning and electrical stimulation therapy comprising an orthopedic lumbar support pillow for a person and a cover that fits over the orthopedic device, the cover having a network of eyelets arranged in spaced apart rows and columns, and a plurality of electrode pads, wherein the electrode pads are positionable at user selected locations relative to the cover and independently of the orthopedic device, such that to correspond to a person's lumbar area, the orthopedic lumbar support pillow's shape, and areas determined by a user before use of the system as being in need of electrical stimulation therapy while musculoskeletal aligning and positioning is provided by the orthopedic lumbar support pillow, wherein the eyelets allow the passage of wires electrically connecting the plurality of electrode pads with an electrical source, and wherein contact between the plurality of electrode pads and the person's lumbar area is achieved by the person resting on top of the plurality of electrode pads, cover, and orthopedic lumbar support pillow, such that the person's weight assists in creating the contact between the plurality of electrode pads and the person's lumbar area.

\* \* \* \* \*